(12) United States Patent
Rossen et al.

(10) Patent No.: US 8,716,481 B2
(45) Date of Patent: May 6, 2014

(54) PROCESS FOR THE PREPARATION OF 6-SUBSTITUTED-1-(2H)-ISOQUINOLINONES

(75) Inventors: Kai Rossen, Frankfurt am Main (DE); Hermut Wehlan, Frankfurt am Main (DE); Oliver Plettenburg, Frankfurt am Main (DE); Volker Kraft, Frankfurt am Main (DE); Guenter Billen, Frankfurt am Main (DE); Simon Gessler, Frankfurt am Main (DE)

(73) Assignee: Sanofi, Paris (FR)

( * ) Notice: Subject to any disclaimer, the term of this patent is extended or adjusted under 35 U.S.C. 154(b) by 632 days.

(21) Appl. No.: 12/817,591

(22) Filed: Jun. 17, 2010

(65) Prior Publication Data

US 2011/0021779 A1    Jan. 27, 2011

Related U.S. Application Data

(63) Continuation of application No. PCT/EP2008/010998, filed on Dec. 22, 2008.

(30) Foreign Application Priority Data

Dec. 26, 2007  (EP) .................................... 07291622

(51) Int. Cl.
*C07D 217/24*    (2006.01)
(52) U.S. Cl.
USPC ....................................................... 546/141
(58) Field of Classification Search
None
See application file for complete search history.

(56) References Cited

U.S. PATENT DOCUMENTS 3,732,245 A    5/1973    Batcho et al.

FOREIGN PATENT DOCUMENTS

| WO | WO 2007/012421 A1 | * | 2/2007 |
| WO | WO2007012421 |   | 2/2007 |
| WO | WO 2007/065916 A | * | 6/2007 |
| WO | WO2007065916 |   | 6/2007 |

OTHER PUBLICATIONS

Fischer et al, Helvetica Chimica Acta, (1990), vol. 73(4), pp. 763-781.*
Fischer, Ulf, et al., "Tricyclic pyridine derivatives with high affinity to the central benzodiazepihne receiptor", Helvetica Chimica Acta, 73(4), 763-81 Coden: HCACAV; ISSN: 0018-019X, 1990.
Watson, C.Y., et al., "Synthesis of 3-substituted benzamides and 5-substituted isoquinolin-1(2H)-ones and preliminary evaluation as inhibitors of poly(ADP-ribose) polymerase (PARP)." Bioorganic & Medicinal Chemistry Jun. 1998, vol. 6, No. 6, Jun. 1998, pp. 721-734.
Bredereck H. et al., Chemische Berichte, Verlag Chemie GmbH, Weinheim, DE. vol. 101, Jan. 1, 1968. [ages 4048-4065—English Abstract Included.
International Preliminary Report on Patentability to PCT/EP2008/010998 dated Jun. 29, 2010.
Written Opinion of the International Searching Authority to PCT/EP2008/010998 dated Mar. 13, 2009.
International Search Report to PCT/EP2008/010998 dated Mar. 13, 2009.
European Search Report to EP072910622.4 dated Jun. 6, 2008.

* cited by examiner

*Primary Examiner* — Zinna Northington Davis
(74) *Attorney, Agent, or Firm* — Scully, Scott, Murphy & Presser, PC

(57) ABSTRACT

The present invention relates to a process for making 6-substituted-1-(2H)-isoquinolinone derivatives of formula (I)

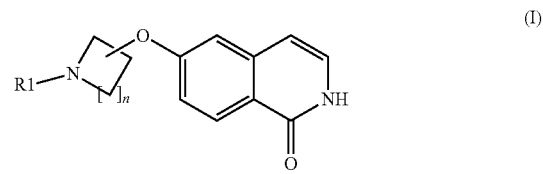

(I)

wherein R1 and n are as described in the specification. The present invention further relates to novel intermediates which are used in the process according to the invention and to processes for preparing such intermediates.

11 Claims, No Drawings

PROCESS FOR THE PREPARATION OF 6-SUBSTITUTED-1-(2H)-ISOQUINOLINONES

CONTINUING DATA

This application is a CON of PCT/EP2008/010998 filed Dec. 22, 2008.

The present invention relates to a process for making 6-substituted-1-(2H)-isoquinolinone derivatives of formula (I)

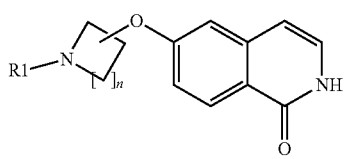

wherein R1 and n are as described in the specification. The present invention further relates to novel intermediates useful in the process according to the invention and to processes for preparing such intermediates.

The derivatives of formula (I) are useful as intermediates in the preparation of inhibitors of the enzyme Rho-Kinase, which are beneficial for the treatment of inter alia, hypertension. Such derivatives are described e.g. in WO 2007/012421 or WO 2007/065916.

The synthetic routes and intermediates described in the prior art are suitable to prepare such compounds and have the additional benefit of introducing diversity late in the synthetic sequence by adding the N-heterocycloalkoxy group to the isoquinolinone at the end of the synthesis. However, one of the described routes performs a high temperature Curtius rearrangement/electrocyclization approach for cyclization to make the isoquinolinone ring wherein the acyl azide proved to be a highly energetic compound making this reaction difficult to handle (basic ring formation reaction shown in Scheme 1).

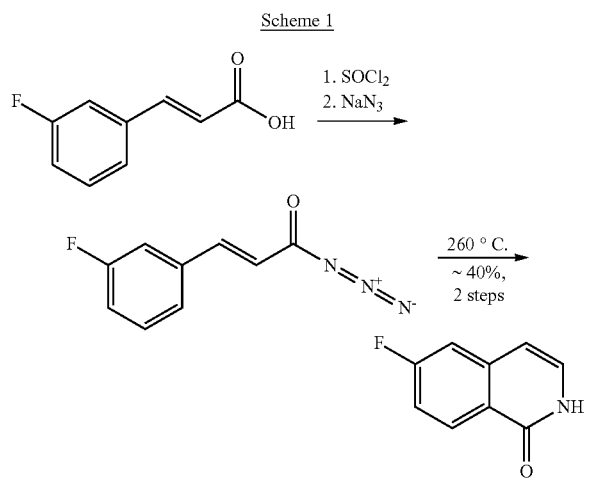

Scheme 1

An alternative route described initially forms an isoquinoline, which is subsequently transformed into the isoquinolin-1-one via formation of the N-oxide and rearrangement. Such an N-oxide also proved to be a highly energetic compound difficult to handle.

In addition both sequences are long and low yielding. They also require the use of protection/deprotection sequences that are reducing the yield of the product.

Accordingly, it is the object of the present invention to provide an alternative route for the preparation of these derivatives. The problem has been solved by the present invention and a new synthetic route is provided, which allows the preparation of a compound of formula (I) in a few chemical reaction steps under the described reaction conditions in good yield with readily available starting materials and reagents. These derivatives may be used itself as Rho-kinase inhibitors or may be used as an intermediate in the synthesis of further inhibitors by modifying the amino group in these compounds by adding further substituents to the N-atom or by modifying any other position in the isoquinolinone system.

In an embodiment the present invention relates to a process for the preparation of a compound of formula (I)

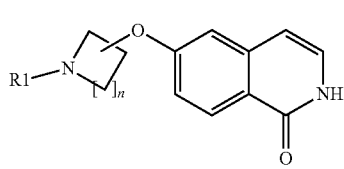

or a salt thereof,
wherein
n is 1, 2, 3 or 4; and
R1 is H or a protecting group,
comprising the steps of
(A) reacting a compound of formula (II)

$$\text{(II)}$$

(structure: X and CH3 substituents on benzene with CN group)

wherein X is halogen,
in a suitable solvent and in the presence of a base with a compound of formula (III)

$$\text{(III)}$$

(structure: R1—N azetidine with OH)

wherein
R1 is H or a protecting group and
n is 1, 2, 3 or 4,
to give a compound of formula (IV)

$$\text{(IV)}$$

(structure: R1—N azetidine—O—benzene(CH3)—CN)

wherein
R1 is H or a protecting group and
n is 1, 2, 3 or 4;
and, if R1 is H, protecting the amino group to give a compound of formula (IV) wherein R1 is a protecting group;
(B) reacting a compound formula (IV), wherein R1 is a protecting group, with a compound of formula (V)

wherein
R$_4$ is —O(C$_1$-C$_6$)alkyl, and
R$_5$ is (C$_1$-C$_6$)alkyl,
to yield a compound of formula (VI)

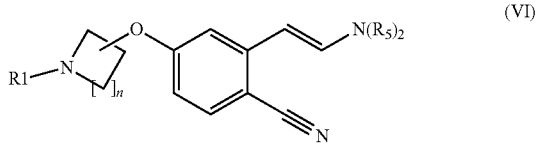

wherein R1 is a protecting group and
n is 1, 2, 3 or 4;
(C) cyclizing a compound of formula (VI) and optionally removing the protecting group in a suitable solvent and in the presence of a hydrohalic acid to give a compound of formula (I)

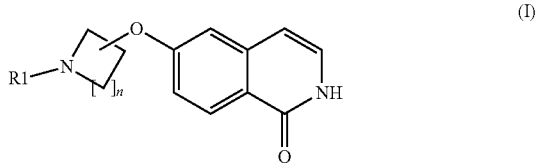

wherein R1 is H or a protecting group;

(D) optionally removing the protecting group from a compound of formula (I) obtained in step (C), wherein R1 is a protecting group, to give a compound of formula (I) wherein R1 is H, and
(E) optionally converting a compound of formula (I) into a salt thereof.

The term alkyl and the corresponding alkylene substituents as used are understood as a hydrocarbon residue which can be linear, i.e. straight-chain, or branched and has 1, 2, 3, 4, 5 or 6 carbon atoms, respectively, as indicated in e.g. (C1-C6)alkyl or (C1-C4)alkyl or (C1-C2)alkyl. This also applies if an alkyl group occurs as a substituent on another group, for example in an alkoxy group (O-alkyl) or an alkoxycarbonyl group or an arylalkyl group. Examples of alkyl groups are methyl, ethyl, propyl, butyl, pentyl (amyl) or hexyl, the n-isomers of all these groups, or the branched isomers isopropyl, isobutyl, 1-methylbutyl, isopentyl, neopentyl, 2,2-dimethylbutyl, 2-methylpentyl, 3-methylpentyl, isohexyl, sec-butyl, tert-butyl (1,1-dimethylethyl) or tert-pentyl (1,1-dimethylpropyl, tert-amyl). Corresponding alkylene groups are methylene, ethylene, propylene and the like.

Halogen means fluoro (F), chloro (Cl), bromo (Br) or iodo (I).

Aryl means phenyl or naphthyl, preferably phenyl, unsubstituted or substituted with one, two or three, preferably one, substituents independently selected from (C1-C4)alkyl, O(C1-C4)alkyl or halogen.

In an alkylenearyl group such as -(C1-C4)alkylenearyl or methylenearyl the alkylene may be substituted one, two or three times by an aryl on the same or different carbon atoms. Alkylenearyl includes e.g. phenylmethylene (also designated benzyl), (triphenyl)methylene (also designated trityl), (diphenyl)methylene (also designated benzhydryl) or (4-methoxyphenyl)-diphenylmethylene.

The process of the present invention to make a compound of formula (I) as well as the single reaction steps (A), (B) and (C), which itself are also an embodiment of the present invention, are summarized in the following scheme. Optionally, a separate deprotection step (D) may be added.

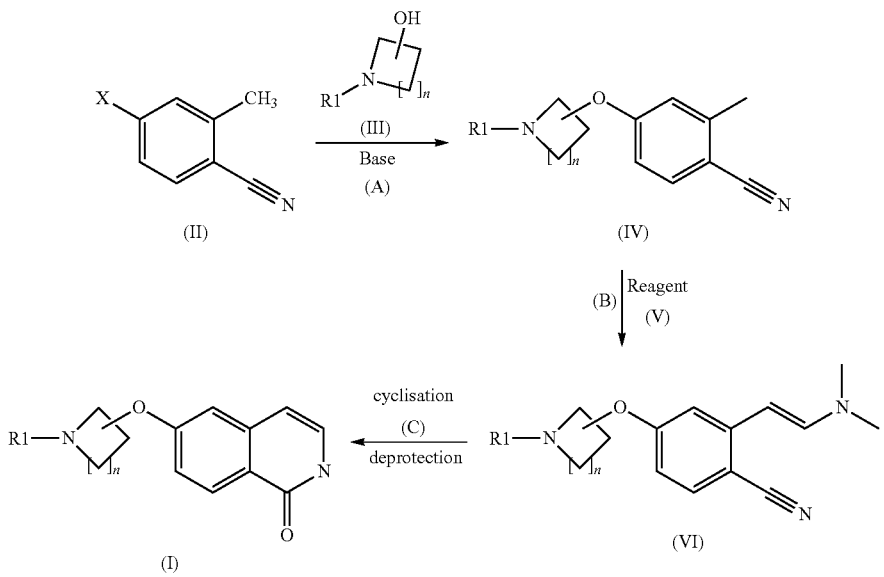

The process steps shown in the Scheme 2 are described in detail below.

Step A

For preparing a compound of formula (IV) a nucleophilic aromatic substitution is used. The 2-methyl-4-halo benzonitrile (II) contains appropriate functionality to build up the required 6-heterocycloalkoxy-1-(2H)-isoquinolinone (VI). The 2-methyl-4-halo benzonitriles are well known in the art and commercially available from multiple vendors, e.g. Sigma Aldrich. In an embodiment of compound (II) the halogen X is selected from fluoro, chloro or bromo, more preferably from fluoro or chloro, most preferably X is fluoro.

The various N-heterocycloalkylalcohols of formula (III) such as 2-hydroxyazetidin (n is 1), 3-hydroxypyrrolidine (n is 2), 3-, or 4-hydroxypiperidine (n=3) and 4-hydroxyazepane (n=4) are commercially available. The N-protected derivatives for use in the reaction step (A) can be prepared according to chemistry known in the art for introducing protecting groups at a secondary amine nitrogen.

A preferred alcohol of formula (III) is 1-Benzyl-3-pyrrolidinol, 3-Hydroxy-piperidine-1-carboxylic acid tert-butyl ester, 1-Benzhydryl-azetidin-3-ol or 4-Hydroxy-piperidine-1-carboxylic acid tert-butyl ester.

Nucleophilic aromatic substitution of the halogen atom X in a compound of formula (II) by an R1-substituted-N-heterocycloalkyl-alkoxide prepared from a compound of formula (III) delivers the compound (IV). The nucleophilic aromatic substitution is a known reaction, which has precedence to occur with amines and arylfluorides or chlorides to lead to the respective substituted anilines, as long as the aromatic ring carries (preferably multiple) strongly electron withdrawing groups, such as the nitro group.

However, where these conditions are not met, nucleophilic substitution becomes difficult or even does not work. In a compound of formula (II) a lack of reactivity could be caused by the weak electron withdrawing character of the nitrile group, coupled with counteraction of the electron-donating methyl group. As a consequence, instead of the desired nucleophilic aromatic substitution reaction, the reaction of a nitrile with an alcohol takes place and gives the alkoxycarboxylate (Pinner reaction). This hydrolysis is described for 4-fluoro-2-methyl benzonitrile in WO 2004/110344 (Astra Zeneca) where classical basic reaction conditions lead exclusively to a reaction at the nitrile instead of the desired nucleophilic aromatic substitution reaction.

Reaction conditions were found which allow a clean and high yielding conversion of 4-halo-2-methyl-benzonitrile (II) and the alcohol (III) to the arylether (IV). The reaction of a compound of formula (II) with a compound of formula (III) to give a compound of formula (IV) is performed in the presence of a base, preferably a strong base, which can be an inorganic or organic base.

Embodiments according to which the reaction may be performed are outlined in the following Scheme 3.

Scheme 3

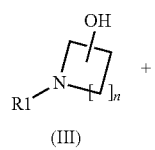

(III)

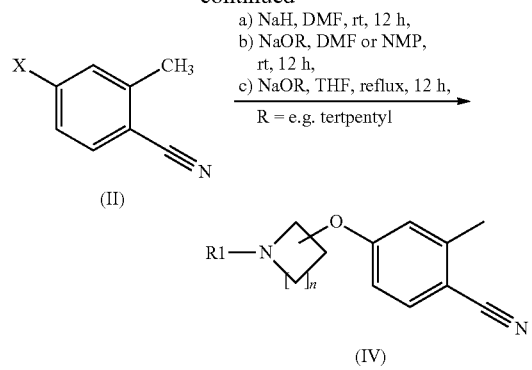

A compound of formula (II), wherein X is halogen is reacted with an alcohol of formula (III), where the range of alcohols is as defined above.

In one embodiment the reaction may be performed with a compound of formula (III) wherein R1 is H, i.e. where the amino group is not protected by a protecting group. In another embodiment R1 is a protecting group. If R1 is a protecting group the protecting group is introduced by known methods in a compound of formula (IV) before step B) is performed. Preferably, R1 is a protecting group in a compound (III). For further embodiments of the protecting group reference is made to the paragraphs following under the heading "Protecting group" below.

The reaction may be performed in various manners wherein the alcohol (III) is converted into an alkoxide using a strong organic or inorganic base in a suitable solvent. In a preferred embodiment the base used in step A) is selected from a tertiary alkali metal alkoxide, alkali metal hydride or alkali metal. Alkali metals in these bases or metals per se are in particular lithium, sodium or potassium. A suitable alkali metal alkoxide may be sodium and potassium tert-butoxide or sodium and potassium tert-amylate. Corresponding alkali metal hydrides may be selected from NaH, KH or LiH.

According to variant a) an alkali metal hydride, e.g. NaH or KH, may be used or the metals such as sodium or potassium may directly be used in a suitable solvent such as an ether or an aprotic, dipolar solvent.

According to variant b) alkoxides of tertiary alcohols may be used, which are both strongly basic and non-nucleophilic due to the strong steric hindrance. Examples are the commercially available sodium and potassium tert-butoxide or sodium and potassium tert-amylate.

The alcoholate may also be made from a base such as sodium or potassium hydroxide and the alcohol, such as tert-butanol or tert-amylalcohol, coupled with a direct or azeotropic distillative removal of water formed to directly form the alkoxide.

In a embodiment the base is a tertiary alkali metal alkoxide. Preferably the base is selected from sodium or potassium tert-butoxide (KOtBu), sodium or potassium tert-amylate or NaH. In a more preferred embodiment potassium tert-butoxide or potassium-tert-amylate are used as bases, most preferably potassium tert-butoxide.

Preferably, the use of solvents is minimized, but for operational ease and convenience suitable solvents could be applied in practice. Solvents which can be used in this reaction step, including variants a) and b) described above, are ethers such as Tetrahydrofuran (THF), 2-Methyl-THF, Methyl-tertbutyl ether (MTBE), Dioxane, Dimethoxyethane (DME) or Dimethoxymethane as well as dipolar aprotic solvents like Dimethylsulfoxide (DMSO), N-Methyl pyrrolidone (NMP), N-Ethyl pyrrolidone, Dimethyl formamide (DMF) or Dimethyl acetamide.

The temperature used is usually in the range of 4° C. to 220° C., preferably in the range of 80° C. to 200° C. and more preferably in the range of 40° C. to 140° C. When using lower boiling solvents, it is possible to perform the reaction under pressure in an autoclave.

Overall the reaction time depends on the solvent, base and reaction temperature used and is conveniently adjustable to these parameters.

The compounds of formula (IV) can be isolated and purified by standard synthetic procedures, such as a direct precipitation from the reaction mixture by the addition of a antisolvent, which precipitates the product from a solution, to the reaction mixture or by a standard aqueous work-up with an extraction into an organic phase and the removal of salts in the aqueous phase. Subsequently, it is possible to crystallize the product. In some instances it may be preferable to purify and isolate the desired product by chromatography.

Step B

In this process step the methyl group in a compound of formula (IV) is reacted with a formylating agent to convert the methyl group into a formyl-methyl group or a synthetic equivalent thereof, such as the enamine or an enolether.

The formylation of 2-methyl-nitrobenzene and derivatives thereof with dimethyl formamide acetals is the known starting point for the so called Leimgruber-Batcho indole synthesis (Leimgruber, W.; Batcho, A. D. U.S. Pat. No. 3,732,245), where a strongly electron-withdrawing nitro group serves to acidify the methyl group in the ortho position. Mild formylation with N,N-dimethylformamide dimethylacetal converts the methyl group to a beta-dimethylamino-styrene, which collapses to the indole on reduction of the nitro group to the amine (Scheme 4).

Scheme 4

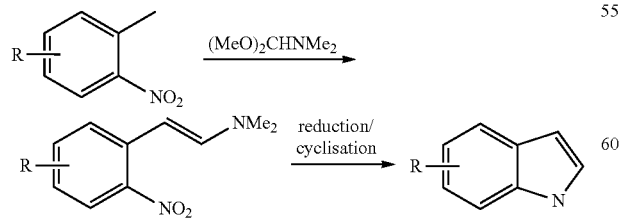

However, the substitution in a 4-heterocycloalkoxy-2-methyl benzonitrile of formula (IV) is such that an analogous outcome would not be predicted by a person skilled in the art.

First, the nitrile group is significantly less electron withdrawing than the nitro group. In addition, the necessary acidity of the methyl group in a 4-heterocycloalkoxy-2-methyl benzonitrile is reduced as a result of the strongly electron-donating 4-heterocycloalkoxy group introduced in the previous step.

As shown in Scheme 4a it is known from U.S. Pat. No. 3,732,245 that the formylation reaction depends highly on the phenyl substituents, even for the strongly activating nitro group.

Scheme 4a

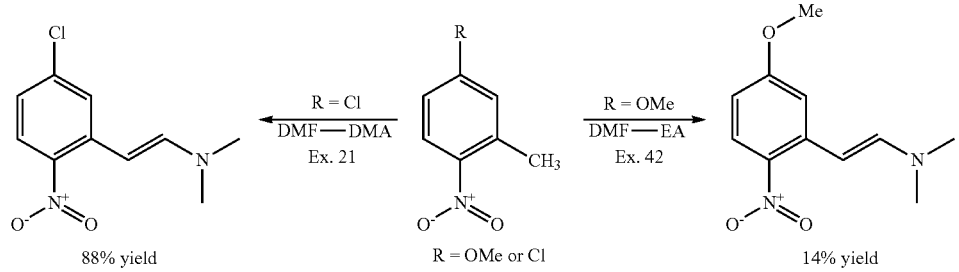

U.S. Pat. No. 3,732,245 discloses that exchanging the mildly activating Cl (Ex. 21, dimethylformamide dimethylacetal (DMF-DMA) as reagent), with the deactivating methoxy group (Ex. 42, dimethylformamide ethylene acetal (DMF-EA) as reagent) leads to a drastic reduction in the observed yield from an attractive 88% (R=Cl) to synthetically barely useful 14% (R=OMe). The O-Me group is identical to the heterocycloalkoxy group (III) used in the present invention for the purpose of electronic deactivation.

Additionally, it is known that the acidifying effect of a nitro group is significantly more pronounced than that of a nitrile group. While quantitative data are missing in the literature for the ortho substitution, the pka values of the methyl group of a toluene substituted with $NO_2$ or CN, respectively, in the para position have been determined experimentally (Table 1 on page 1818 in J. Org. Chemistry 42, No. 10, 1977). Based on these measurements, the activating effect of the CN group is drastically reduced by 10 pKa units (—$NO_2$ pK 20.4; —CN pK 30.8) and is so weak that it is barely measurable. Consequently, it is expected that 2-methyl benzonitriles are significantly less reactive than the corresponding 2-methyl nitrobenzenes used in U.S. Pat. No. 3,732,245.

The formylation for a methyl substituted benzonitrile was actually reported by Bredereck, H. et al. in Chem. Berichte 1968, 101, 4048-4056. In this case another formylating reagent (t-BuOCH(NMe$_2$)$_2$) was used.

However this transformation was performed with ortho- and para-Tolunitril only with moderate yield (Table 1, pages 4050/4051) confirming the above observation on the low reactivity of a CN group (see Scheme 4b, reaction with t-butylO—CH—N(NMe$_2$)$_2$).

Scheme 4b

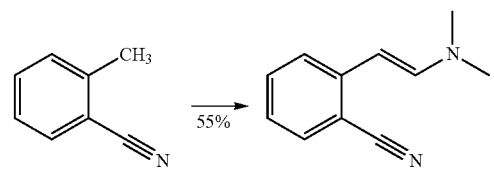

With some activation (Cl in the para position) the reaction works better with t.-butylO—CH—N(NMe$_2$)$_2$ (Widmer, U. Helv. Chim. Acta 1990, 73, 763).—see Scheme 4c Scheme 4c

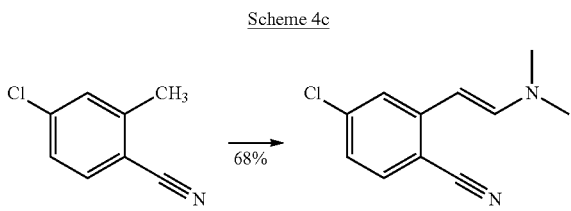

Generally this transformation is described in the literature as working acceptably for special situations only in cases where the methyl group is doubly activated by two nitriles (WO 2005/123680; Threadgill, M. D. et al. Bioorg. Med. Chem. 1998, 6, 721) or by a nitrile and a nitro group (U.S. Pat. No. 6,906,192; Glossop, S. C Synthesis 2007, 981; Cannon, J. G. et al. J. Heterocyc. Chem. 1983, 20, 149).

As discussed previously, this is rather different from having a single nitrile and a strongly deactivating alkoxy group as in the 4-heterocycloalkyloxy-2-methyl benzonitrile of formula (IV). Extrapolating from the examples given in U.S. Pat. No. 3,732,245 (see Scheme 4a), and knowing that a CN group is quite weak in activating the methyl group, it is expected that the diminished reactivity of 2-methyl benzonitriles (see scheme 4b) is reduced even further by the N-heterocyclylalkoxy group in para position to the nitrile and that the reaction will not work or, if at all, will work with such a low yield to be not synthetically useful, especially for a large scale synthesis.

Therefore, a formylation reaction would not be considered by a skilled person for the synthesis of such kind of compound (scheme 4d) with the reagents described in the literature above.

Scheme 4d

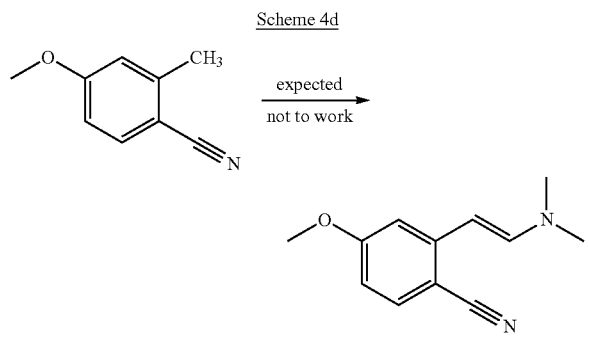

Consequently and in line with this expectation, the initial attempts by the inventors to utilize Leimgruber-Batcho-indole synthesis-like conditions with various dimethylformamide dialkoxyacetals according to U.S. Pat. No. 3,732,245 were met with failure, leading to no conversion or to a complex reaction mixture under more forcing conditions. Potential alternative formylations by metalation or use of strong organic bases like LDA or potassium hexamethyldisilazide (KHMDS) and quench with formylation agents such as DMF, Vilsmeyer reagent or ethyl formate failed to deliver more than traces of the desired product, which would lead to the conclusion that the combination of a weakly activating group, such as a nitrile, with a deactivating group, such as an alkoxy group, is not sufficient to perform this reaction.

Surprisingly, it was found that it is possible to obtain excellent conversion of a 4-heterocycloalkoxy-2-methyl benzonitrile (IV) to the dimethylaminoenamine (VI) in good yield by using a reagent of formula (V).

The overall reaction of this step is shown in Scheme 5 wherein an alcohol of formula (IV) with n being 3 is shown by way of example.

Scheme 5

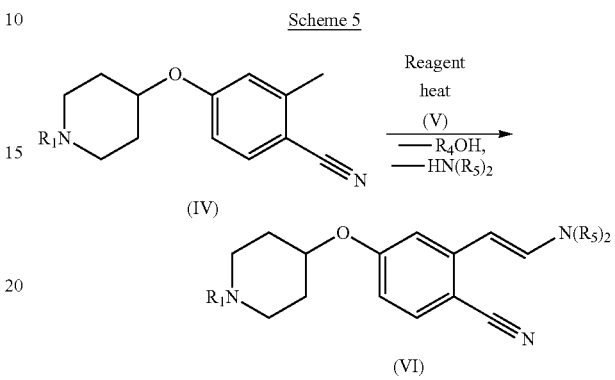

Reagent (V) is a compound of the formula $$R_4\text{—CH[N}(R_5)_2]_2 \qquad (V)$$

wherein
R$_4$ is —O(C$_1$-C$_6$)alkyl, and
R$_5$ is (C$_1$-C$_6$)alkyl.

In a compound (V) R4 is —O(C$_1$-C$_6$)alkyl, such as methoxy, ethoxy, isopropoxy, tert-butyloxy, or 1,1-dimethylpropyloxy, and R5 is (C$_1$-C$_6$)alkyl, preferably (C$_1$-C$_4$)alkyl, such as methyl or ethyl. Preferably, R4 is —O(C$_1$-C$_6$)alkyl.

In a further embodiment of a reagent (V) R4 is tert-butyloxy or ethoxy, preferably tert-butyloxy. In another embodiment R5 is methyl. In another embodiment of a reagent (V) tert-butyloxy-bis-(dimethylamino)methane is used in the reaction with a compound of formula (IV).

A particular preferred compound R$_4$—CH[N(R$_5$)$_2$]$_2$ (V) is tert-butyloxy-bis-(dimethylamino)methane. This reagent (R$_4$ is tert-butyloxy, R5 is methyl) is commercially available (also designated Bredereck's reagent). Similar active formylation reagents (V), such as tert-butyloxy-bis-(diethylamino)methane (R$_4$ is tert-butyloxy, R$_5$ is ethyl) or tert-pentoxy-bis-(dimethylamino)methane (R4 is 1,1-dimethyl-propyloxy, R$_5$ is methyl) are useful for the reaction as well and can be utilized. Such reagents are commercially available from various suppliers, such as Aldrich, Acros or Fluka or can be synthesized by known procedures as described by Bredereck in Chem. Berichte 1968, 101, 41 or Wasserman in J. Org. Chem. 1985, 50, 3573. The reagent (V) is known to possibly interconvert under the reaction conditions (see, for e.g. Bredereck in Chem. Berichte 1968, 101, 51-57) and these intermediates or species are included in the definition and scope of the reagent (V).

In one embodiment of the reaction the alcohol formed by the reaction of the formylation reagent R$_4$—CH[N(R$_5$)$_2$]$_2$, with a compound of formula (IV) (e.g. tert-butanol, if R$_4$ is tert-butyloxy) is concomitantly removed at high temperature. Reagent (V) is unstable at high temperature. Therefore, in another embodiment of the reaction, the reaction conditions can be chosen such that the reagent (V) is continuously added to a hot solution of a compound of formula (IV) with distillative removal of the alcohol (e.g. tert-butanol) prepared when the reaction proceeds.

Reagent (V) may also be used as a solvent to which a compound of formula (IV) may be added directly without prior dilution in a solvent. Alternatively a compound of formula (IV) may be diluted in a suitable solvent, such as N-methylpyrrolidone or a lower boiling ether, such as MTBE (methyl-tert-butylether), that is continuously removed by distillation.

The temperature used for performing the reaction is in a range of 80°-200° C., preferably 90°-180° C., more preferably 110-170° C. A base such as sodium- or potassium-tertbutylate or sodium- or potassium-tertamylate or DBU (1,8-Diazabicyclo[5.4.0]undec-7-en) may be added to facilitate the reaction.

The amount of reagent (V) is not critical and may vary from 1 to 30 Mol-equivalents. More preferably 3 to 10 Mol-equivalents of the reagent are used.

The product obtained can be isolated and further purified by standard synthetic techniques, preferred is the addition of an antisolvent to the hot reaction mixture and the direct filtration of the precipitated product. For example addition of ethanol to the hot reaction mixture may lead to the precipitation of some of the desired product. Equally attractive is the evaporation of the reaction mixture followed by a regular aqueous work-up and a subsequent crystallization of the product. Furthermore, the product may be isolated by chromatography by known methods.

Alternatively, the product contained in the reaction mixture may also be directly used without further purification in the next reaction step, i.e. reaction steps (B) and (C) may be performed as a single-pot reaction. For control of impurities and overall process-robustness isolation of the intermediate is advantageous.

While the stereochemistry of the enamine in (VI) is drawn as E-isomer, it may exist as both E and Z isomer, which are synthetically equivalent.

A protecting group R1 can be chosen from a group as outlined under "Protecting group" below.

Step C, D and E

According to the process step C) of the present invention a compound of formula (VI)

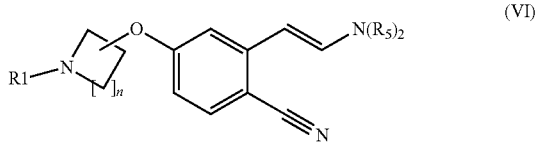

is cyclized and the protecting group is optionally removed in a suitable solvent and in the presence of a hydrohalic acid to aive a compound of formula (I)

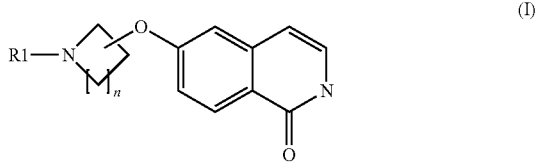

wherein R1 is H or a protecting group;
(D) optionally the protecting group is removed from a compound of formula (I) obtained in step (C), wherein R1 is a protecting group, to give compound a formula (I) wherein R1 is H, and (E) optionally, a compound of formula (I) is converted into a salt thereof.

The transformation of 4-heterocycloalkoxy-2-(2'-dialkylaminovinyl)benzonitriles of formula (VI) to 6-heterocycloalkoxy-1-(2H)-isoquinolinones of formula (I) is not described in the literature. Conditions and cyclization reagents were found that furnished the desired 6-heterocycloalkoxy-1-(2H)-isoquinolinone (I). These cyclization conditions and reagents used therein are part of the present invention.

In an embodiment, the cyclization reaction of 4-heterocycloalkoxy-2-(2'-dialkylaminovinyl)benzonitriles of formula (VI) to a compound of formula (I) can be performed by reacting a compound of formula (VI) in the presence of a strong acid as cyclizing reagent, i.e. to perform the reaction under acidic reaction conditions. Under acidic conditions it is understood to perform the cyclization reaction in the presence of a hydrohalic acid such as HCl, HBr or HI, preferably HCl, in a suitable solvent such as an alcohol, especially using a $(C_1-C_6)$-alkanol as solvent such as methanol, ethanol, propanol, butanol or pentanol. Both the n-alcohols as well as the isomers can be used. Preferably, the reaction is performed in methanol, ethanol, n-propanol or n-butanol, with n-butanol being most preferred.

In one embodiment a larger alcohol from the group of $(C_1-C_6)$alkanols, such as a $(C_4-C_6)$alkanol, including butanol, instead of methanol or ethanol described in the literature is used. This is advantageous for preparing a compound of formula (I). With such alcohols the reaction can be performed at a higher temperature. At elevated temperatures the reaction proceeds much better and less impurities are formed. Inherent by-products such as dimethylammonium-chloride and the corresponding alkyl chloride, which is generated from the alcohol, remain in solution, whereas the product of formula (I) or a salt thereof has a low solubility and tends to precipitate from the reaction mixture. The precipitated product can usually be isolated by filtration in excellent yield and high purity.

As a source for a hydrohalic acid gaseous HCl or HBr or HI may be used and added to the alcohol. As an alternative to the use of gaseous HCl, other reagents, such as TMSCl or AcCl (acetylchloride), which react with an alcohol to form an anhydrous alcoholic HCl solution, can also be used. A preferred set of reaction conditions for cyclization involves the use of gaseous HCl in a $(C_1-C_6)$-alkanol, preferably n-butanol, as solvent.

The reaction is preferably performed in a temperature range of 40° C. to 140° C., more preferred the temperature range is 60° C. to 120° C., depending on the boiling point of the alcohol used.

The reaction is preferably performed using 2 to 30 Mol-equivalents of the hydrohalic acid, such as gaseous HCl, more preferably by using 3 to 15 Mol-equivalents. On a technical scale, the excess of the hydrohalic acid such as HCl can be easily neutralized in a basic scrubber.

In the cyclization reaction the protecting group may optionally also be removed simultaneously to obtain a compound of formula (I) wherein R1 is H. On the choice of the protecting group in R1 to obtain a compound of formula (I) wherein R1 is H or a protecting group see the next paragraphs on the "Protection group".

Protecting Group

The protecting group useful in one of the above mentioned reaction steps A), B) and C) and in the corresponding intermediates can be selected from a variety of groups e.g. listed in but not limited to those mentioned in: T. W. Greene and P. G.

M. Wuts: Protective Groups in Organic Synthesis, Third Edition, John Wiley and Sons, New York, 1999 Chapter 7, page 494.

The protecting group in R1 is preferably one which is stable under the basic reaction conditions used in step A) and B).

Suitable stable protecting groups R1 useful in step A) and also steps B) and C) and in the intermediates (III), (IV) and (VI) can be selected from carbamates such as tert-butyloxycarbonyl and benzyloxycarbonyl or p-methoxybenzylcarbonyl, amides such as formyl or acetyl, N-alkylenearyls such as benzyl, (diphenyl)methylene, trityl or (4-methoxyphenyl)diphenylmethylene or N—P and N-sulfonyl protecting groups such as dialkyl phosphoramidates and p-toluenesulfonyl.

The protecting group can be introduced by methods known in the art whereby a N-heterocycloalkylalcohol of formula (III), wherein R1 is H, is reacted with a corresponding protecting group providing reagent to deliver the protected amine. In another embodiment, the protecting group may be introduced in a compound of formula (IV), if R1 is H in a reaction of step A) as outlined above.

Accordingly, in an embodiment the protecting group R1 in a compound of formula (III), (IV) or (VI) or (I) is a residue selected from —C(O)—R6 wherein R6 is H, $CH_3$, tert-butyloxy-, benzyloxy- or p-methoxybenzyl-, or $R_1$ is —$(C_1$-$C_4)$ alkylenearyl, preferably methylenearyl, such as benzyl, (diphenyl)methylene, (triphenyl)methylene or (4-methoxyphenyl)-diphenylmethylene, or $R_1$ is —$S(O)_2$-aryl, such as p-toluenesulfonyl, or $R_1$ is —$P(O)(O(C_1$-$C_6))_2$ or—$P(O)(OAryl)_2$.

Suitable reagents to be used for introducing the protecting are know in the art and are commercially available. For example, Di-tert-butyl-dicarbonate may be used for introducing the tert-butyloxycarbonyl group. The choice of the individual group is determined by the availability of the starting material as well as other useful properties, such as stability under the other reaction conditions, ease of subsequent removal and crystallinity of intermediates.

Preferably the same protecting group is used throughout the synthesis. Accordingly a protecting group stabile under basic reaction conditions is preferably used in steps A) and B) and C). For obtaining a deprotected product of formula (I) in step (C), wherein R1 is H, the protecting group may be either acid-labile or acid-stable.

In one embodiment of the cyclization reaction in step C) of a compound of formula (VI) to obtain a compound of formula (I) the protecting group may optionally be removed simultaneously during the cyclization reaction to yield a compound of formula (I) wherein R1 is H. In this embodiment an acid-labile protecting group is preferably used. Accordingly, a compound of formula (I) may directly be obtained from a compound of formula (VI) without containing a protecting group thus giving a compound of formula (I) wherein R1 is H. This group can be simultaneously cleaved of in the same reaction step where the cyclization reaction takes place and a compound of formula (I) is directly obtained in step C) wherein R1 is H.

Suitable acid labile protecting groups useful in this embodiment are groups wherein R1 is a carbamate (R1 is —C(O)—R6 wherein R6 is tert-butyloxy, benzyloxy or p-methoxybenzyl) such as tert-butyloxycarbonyl or benzyloxycarbonyl, an amide such as N-formyl (R6 is H) or N-acetyl (R6 is —$CH_3$), or R1 is —$(C_1$-$C_4)$alkylenearyl, preferably methylenearyl, such as Trityl((triphenyl)methylene), (4-methoxyphenyl)diphenylmethylene or p-methoxybenzyl. Such groups can be removed, i.e. converted into the amino group, by methods known in the art. These protecting groups are stabile under the base reaction conditions in steps A) and B) but are acid-labile in step C). The Boc (tert-butyloxycarbonyl) group in R1 is preferred when a hydrohalic acid is used for cyclization of a compound of formula (VI) as outlined above.

In a particular embodiment of the present invention an acid labile protecting group, preferably the tert-butyloxycarbonyl group, is used as a protecting group in R1 in a compound of formula (III), (IV) and (VI). More particular, where tert-butyloxycarbonyl is used in R1, the cyclization reaction of a compound of formula (VI) is preferably done with a hydrohalic acid such as HCl, preferably gaseous HCl, in a suitable solvent, preferably in n-butanol, which gives directly a compound of formula (I) wherein R1 is H. With the use of an acid labile group step (D) can be omitted.

In another embodiment of the cyclization reaction of a compound of formula (VI) a protecting group may be used in the preparation of a compound of formula (I), wherein a cyclization product of formula (I) is obtained which still contains the protecting group. Suitable protecting groups, which remain at the nitrogen under the acidic reaction conditions and can be used for cyclization of a compound of formula (VI) are groups wherein R1 is an (C1-C4)alkylenearyl, such as benzyl or (diphenyl)methylene, a carbamate, such as methyl- or ethyloxycarbonyl (R1 is —C(O)R6 with R6 being —$OCH_3$ or —$OCH_2CH_3$), or a N-sulfonyl group where R1 is —$S(O)_2$-aryl such as p-toluenesulfonyl. If desired, the corresponding protecting group is optionally removed separately by known methods in step (D) to give a compound of formula (I) wherein R1 is H.

Accordingly, where a protecting group in R1 and cyclization conditions are used wherein the protecting group remains in the cyclization product and ends up within R1 in a compound if formula (I), the protecting group may optionally be removed later by standard procedures well known in the art taking the chemical reactivity of the protecting group used into account. For example the benzyl group may be removed by hydrogenolysis.

Where it is desirable that the protecting group is removed after the reaction step (C), the removal of the protecting group may be done in a separate step (D) with prior isolation of the intermediate containing the protecting group or the reaction mixture obtained after the cyclization reaction may directly be used in the deprotection step.

In an embodiment a compound of formula (I) is prepared by the process of the present invention wherein R1 is H. In another embodiment a compound of formula (I), wherein R1 is H, is directly prepared in step (C) by removing the protecting group.

A compound of formula (I), wherein R1 is H or a protecting group, preferably H, is optionally converted into a salt thereof. Compound (I) can be directly obtained as a salt if the acid is not removed from the cyclization step in order to obtain the free base. The acid used in the cyclization step may also be removed and exchanged against another acid by known methods to prepare the corresponding salt of a compound of formula (I).

Salts of a compound of formula (I), incl. pharmaceutically acceptable salts, may be prepared from inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, lactic, maleic, malic, methanesulfonic, succinic, p-toluenesulfonic and tartaric acid by methods known in the art.

In another embodiment of the process of the present invention a compound of formula (I), wherein R1 is H, as prepared by the process of the present invention may be used as an intermediate in the synthesis of further derivatives thereof having R1 substituents other than H. Accordingly, the present invention also relates to the use of a compound of formula (I) wherein R1 is H for making Rho-kinase inhibitors. The present invention relates to a process of making a compound of formula (I) wherein R1 is H and, in a second step, a compound of formula (I″) is prepared, wherein R1 becomes R7, by reacting a suitable chemical equivalent of a R7 group with a compound of formula (I). For example a suitable aldehyde R7-C(O)H, wherein R7 is e.g. (C1-C5)alkyl or a further substituted (C1-C5)alkyl group, may be reacted via reductive amination procedure as described in WO 2007/012421 with a compound of formula (I) wherein R1 is H to obtain a (C1-C6)alkyl substituted 6-heterocycloalkoxy-1-(2H)-isoquinolinone (I′).

Compounds of formula (I) containing a protecting group in R1 may also be used as intermediates for further modifications in the isoquinolinone part of the molecule in order to prepare derivatives which may also be suitable as Rho-Kinase inhibitors.

In a further embodiment the present invention relates to a process for the preparation of a compound of formula (IV)

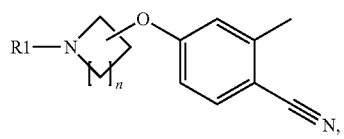

(IV)

wherein R1 is H or a protecting group and
n is 1, 2, 3 or 4;
comprising reacting a compound of formula (II)

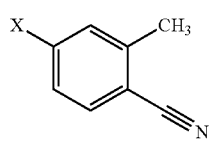

(II)

wherein X is halogen
in a suitable solvent and in the presence of a base, preferably a strong base, with a compound of formula (III)

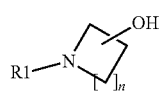

(III)

wherein R1 is H or a protecting group and
n is 1, 2, 3 or 4.

This process corresponds to process step (A) in the synthesis of a compound of formula (I) as described above.

Surprisingly reaction conditions could be found that allowed a clean, high yielding and safe conversion of the 4-halo-2-methyl-benzonitrile (II) and the alcohol (III) to the arylether (IV). According to an embodiment the reaction of a compound of formula (II) with a compound of formula (III) to give a compound of formula (IV) is performed in the presence of a base selected from a tertiary alkali metal alkoxide.

In one embodiment tertiary alkali metal alkoxides which can be used in this reaction step are sodium or potassium tert-butoxide (KOtBu), sodium or potassium tert-amylate. In a preferred embodiment potassium tert-butoxide or potassium tert-amylate are used as a base, most preferably potassium tert-butoxide.

The corresponding alcoholate may also be made from a base such as sodium or potassium hydroxide and the alcohol, such as tert-butanol or tert-amylalcohol, coupled with a direct or azeotropic distillative removal of water formed to directly form the alkoxide.

Moreover, the description and other embodiments mentioned above in connection with the performance of the reaction step (A) also apply here.

In a further embodiment the present invention relates to a process for the preparation of a compound of formula (VI)

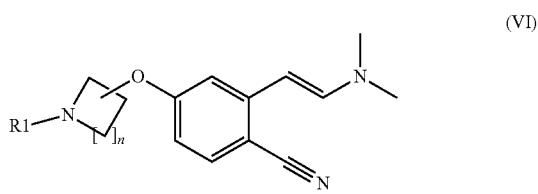

(VI)

wherein R1 is a protecting group and
n is 1, 2, 3 or 4;
comprising reacting a compound of formula (IV)

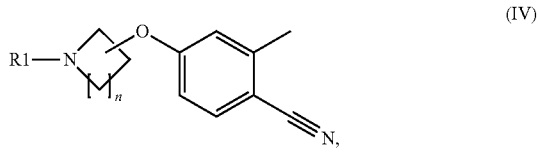

(IV)

wherein R1 is a protecting group and n is 1, 2, 3 or 4;
compound of formula (V)

$$R_4—CH[N(R_5)_2]_2 \quad (V)$$

wherein
$R_4$ is —O($C_1$-$C_6$)alkyl,
$R_5$ is ($C_1$-$C_6$)alkyl,

This process corresponds to process step (B) in the synthesis of a compound of formula (I) described above. Accordingly, the description and embodiments mentioned above in connection with step (B) apply in this embodiment as well. In a preferred embodiment of $R_4$—CH[N($R_5$)$_2$]$_2$ (V), $R_4$ and $R_5$ are as described before. tert-butyloxy-bis-(dimethylamino)methane is a preferred compound (V).

In another embodiment the present invention relates to a process for the preparation of a compound of formula (I)

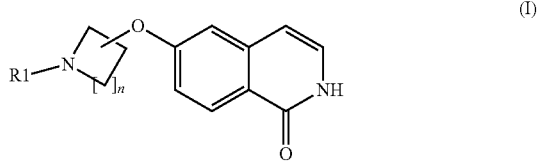

(I)

or a salt thereof, wherein
R1 is H or a protecting group and n is 1, 2, 3 or 4, comprising
C) cyclizing a compound of formula (VI)

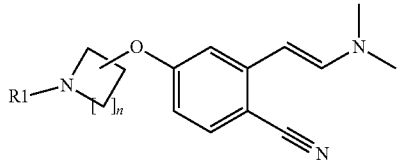

(VI)

wherein R1 is a protecting group and
n is 1, 2, 3 or 4,
and optionally removing the protecting group in a suitable solvent and in the presence of a hydrohalic acid to give a compound of formula (I)

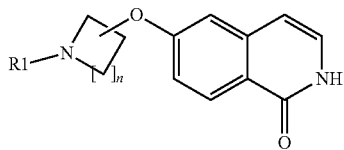

(I)

wherein R1 is H or a protecting group; and
(D) optionally removing the protecting group from a compound of formula (I) obtained in step (C), wherein R1 is a protecting group, to give compound a formula (I) wherein R1 is H, and
(E) optionally, converting a compound of formula (I) into a salt thereof.

This process corresponds to the cyclization step (C) in the above described synthesis of a compound of formula (I). Accordingly the statements and embodiments mentioned above in connection with step (C), (D) and (E) also apply to this process embodiment here.

In a further embodiment the present invention relates to a compound of formula (IV)

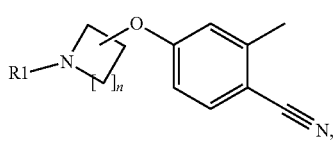

(IV)

wherein R1 is H or a protecting group and
n is 1, 2, 3 or 4.

Compounds of formula (IV) are a further embodiment of the present invention. In particular a compound of formula (IV), is selected from
4-(1-Benzyl-pyrrolidin-3-yloxy)-2-methyl-benzonitrile,
3-(4-Cyano-3-methyl-phenoxy)-piperidine-1-carboxylic acid tert-butyl ester,
4-(1-Benzhydryl-azetidin-3-yloxy)-2-methyl-benzonitrile, or
4-(4-Cyano-3-methyl-phenoxy)-piperidine-1-carboxylic acid tert-butyl ester.

In another embodiment the present invention relates to a compound of formula (VI)

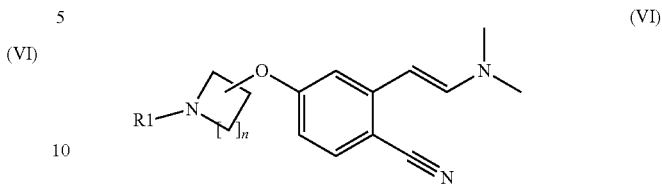

(VI)

wherein R1 is H or a protecting group and.
n is 1, 2, 3 or 4. Preferably, R1 is a protecting group.

The features and embodiments of the protecting group as outlined before apply to a compound (VI). Preferably, the protecting group is tert-butyloxycarbonyl.

In a further embodiment of a compound of formula (VI), the compound is selected from the group of
4-(1-Benzyl-pyrrolidin-3-yloxy)-2-(2-dimethylamino-vinyl)-benzonitrile,
3-[4-Cyano-3-(2-dimethylamino-vinyl)-phenoxy]-piperidine-1-carboxylic acid tert-butyl ester,
4-(1-Benzhydryl-azetidin-3-yloxy)-2-(2-dimethylamino-vinyl)-benzonitrile, or
4-[4-Cyano-3-(2-dimethylamino-vinyl)-phenoxy]-piperidine-1-carboxylic acid tert-butyl ester.

In one embodiment of a compound of formula (IV) or (VI) R1 is a protecting group having the features mentioned above for the protecting group, including being an acid-labile protecting group, preferably selected from a carbamate, such as the tert-butyloxycarbonyl group, benzyloxycarbonyl group or p-methoxybenzylcarbonyl, more preferably tert-butyloxycarbonyl.

In a further embodiment of the present invention, in any of the compounds of formula (I), (III), (IV) or (VI) n is 2 or 3, more preferably n is 3.

The oxygen (O) may be bound to the N-containing ring in any of the compounds of formula (I), (III), (IV) or (VI) in any position via a ring carbon atom. In one embodiment, n is 3 and O is attached to the 4-position of the resulting piperidine ring to give a compound of formula (Ic)

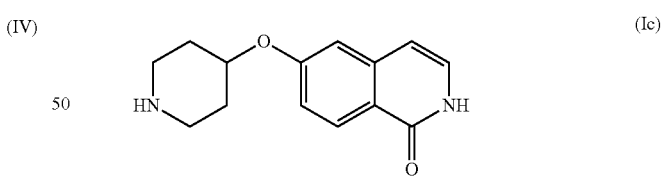

(Ic)

or, in another embodiment, the 0 is attached to the 3-position of the piperidine ring to give a compound of formula (Id)

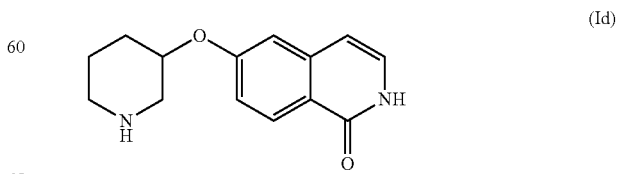

(Id)

in all their stereoisomeric forms.

In another embodiment, the O is attached to the 3-position of the pyrrolidine ring to give a compound of formula (Ie) in all their stereoisomeric forms.

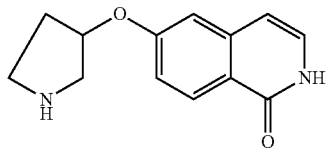
(Ie)

In addition, it is well known in the art that the 2H-isoquinolin-1-ones of formula (I) shown in the schemes can also exist in their tautomeric form as 1-hydroxy-isochinolines and these tautomers are included in the scope of the present invention. Moreover, a compound of formula (I), (IV) or (VI) may contain a chiral carbon atom. Accordingly, these compounds exist in stereoisomeric forms, including enantiomers or diastereomers. These stereoisomeric forms and mixtures of stereoisomeric forms in all ratios are included in the scope of the present invention.

In one embodiment of the process of the present invention 6-(Piperidin-4-yloxy)-2H-isoquinolin-1-one or a salt thereof is prepared. In another embodiment, 6-(Piperidin-3-yloxy)-2H-isoquinolin-1-one or a salt thereof is prepared. In a further embodiment 6-(pyrrolidin-3-yloxy)-2H-isoquinolin-1-one or a salt thereof is prepared. A preferred salt is the hydrochloride salt.

The compounds of the formulae (IV) and (VI) may be used as intermediates in the preparation of Rho kinase inhibitors.

The present invention also relates to the use of a compound of formula (IV)

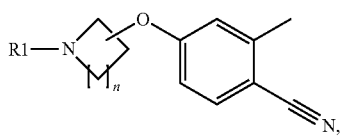
(IV)

or of formula (VI)

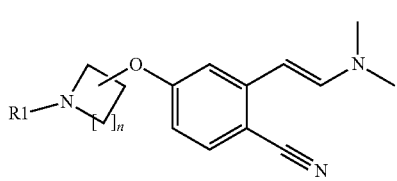
(VI)

wherein R1 is H or a protecting group, preferably R1 a protecting group, and
n is 1, 2, 3 or 4,
in the preparation of a compound of formula (I)

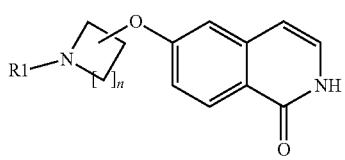
(I)

wherein
n is 1, 2, 3 or 4; and
$R_1$ is H or a protecting group, preferably $R_1$ is H.

EXAMPLES

In the following examples the processes and intermediates of the present invention are outlined in more detail. Accordingly, the following examples are part of the present invention. They are also intended to illustrate but not to limit the present invention.

Abbreviations
rt room temperature
DMF Dimethylformamide
g Gramm
ml Milliliter
H Hours General Procedure (GP) Step A:

The appropriate 4-Fluoro-2-methyl-benzonitrile, dissolved in DMF, was added to a mixture of the appropriate N-heterocycloalcohol of formula (III) and sodium hydride in DMF. The mixture was stirred at room temperature (rt) until the reaction was complete. The reaction was quenched with water. The aqueous layer was extracted with ethylacetate (AcOEt) or methyl tert. butyl ether (MTB ether). The combined organic layers were washed with brine, dried and concentrated to yield the appropriate N-heterocycloalkoxy-2-methyl-benzonitrile.

A1) 5.0 g 4-Fluoro-2-methyl-benzonitrile, 6.6 g 1-Benzyl-pyrrolidin-3-ol and 1.2 g sodium hydride in 85 mL DMF were allowed to react according to GP A to give 9.7 g (90%) 4-(1-Benzyl-pyrrolidin-3-yloxy)-2-methyl-benzonitrile. Mass: Calcd. ($C_{19}H_{20}N_2O$)=292 found:293 (M+H$^+$).

A2) 5.0 g 4-Fluoro-2-methyl-benzonitrile, 7.5 g 3-Hydroxy-piperidine-1-carboxylic acid tert-butyl ester and 1.2 g sodium hydride in 85 mL DMF were allowed to react according to GP A to give 11.1 g (95%) 3-(4-Cyano-3-methyl-phenoxy)-piperidine-1-carboxylic acid tert-butyl ester. Mass: Calcd. ($C_{18}H_{24}N_2O_3$)=316 found: 261 [M+H–t($C_4H_9$)]$^+$ A3) 5.0 g 4-Fluoro-2-methyl-benzonitrile, 8.9 g 1-Benzhydryl-azetidin-3-ol and 1.2 g sodium hydride in 85 mL DMF were allowed to react according to GP A to give 11.9 g (91%) 4-(1-Benzhydryl-azetidin-3-yloxy)-2-methyl-benzonitrile. Mass: Calcd. ($C_{24}H_{22}N_2O$)=354 found:355 (M+H$^+$).

A4) 1.35 g 4-Fluoro-2-methyl-benzonitrile, 2.11 g 4-Hydroxy-piperidine-1-carboxylic acid tert-butyl ester and 0.6 g sodium hydride in 30 mL DMF were allowed to react according to GP A to give 2.6 g (81%) 4-(4-Cyano-3-methyl-phenoxy)-piperidine-1-carboxylic acid tert-butyl ester. Mass: ($C_{18}H_{24}N_2O_3$): calcd. 316, found 261 [M+H–t($C_4H_9$)]$^+$ Alternative Procedure for Step A A5) 4-Hydroxy-piperidine (1.05 g) was dissolved in 7 mL MTBE and 5 mL THF. Potassium tert-butylate (1.43 g) was added and the mixture was heated to 50° C. for 30 min. After cooling to rt, 4-Fluoro-2-methyl-benzonitrile (1.32 g) was added in portions. After stirring at rt for 2 h the reaction was quenched with water. The phases were separated and the aqueous layer was extracted with ethyl acetate (3×10 mL). The combined organic layers were washed with brine (10 mL), dried with MgSO$_4$ and concentrated to yield 1.92 g (94%) 2-Methyl-4-(piperidin-4-yloxy)-benzonitrile. Mass (ESI) ($C_{13}H_{16}N_2O$): calcd. 216, found 217 [M+H]$^+$.

General Procedure (GP) Step B:

The appropriate N-heterocycloalkoxy-2-methyl-benzonitrile was suspended in 2 mol equivalents of tert-butyloxybis(dimethylamino)methane and the mixture was heated between 120 and 170° C. Further amounts of tert-Butyloxybis(dimethylamino)-methane were added until the reaction was complete. After cooling, ethanol was added and the crystalline product was filtered to yield the appropriate N-heterocycloalkoxy-2-((E)-2-dimethylamino-vinyl)-benzonitrile. Alternatively, the solution was evaporated to dryness and the crude product was directly employed in the next step C).

B1) 9.7 g 4-(1-Benzyl-pyrrolidin-3-yloxy)-2-methyl-benzonitrile, 3.2 g sodium tert-butylate and 37 mL tert-butyloxybis(dimethylamino)methane were allowed to react according to GP B to give 15.2 g of crude 4-(1-Benzyl-pyrrolidin-3-yloxy)-2-(E)-2-dimethylamino-vinylybenzonitrile.

B2) 11.1 g 3-(4-Cyano-3-methyl-phenoxy)-piperidine-1-carboxylic acid tert-butyl ester and 37 mL tert-Butyloxybis(dimethylamino)methane were allowed to react according to GP B to give 13.3 g of crude 3-[4-Cyano-3-((E)-2-dimethylamino-vinyl)-phenoxy]-piperidine-1-carboxylic acid tert-butyl ester.

B3) 11.9 g 4-(1-Benzhydryl-azetidin-3-yloxy)-2-methyl-benzonitrile, 3.2 g sodium tert-butylate and 27 mL tert-Butyloxybis(dimethylamino)methane were allowed to react according to GP B to give 13.9 g of crude 4-(1-Benzhydryl-azetidin-3-yloxy)-2-((E)-2-dimethylamino-vinyl)-benzonitrile.

B4) 20 g 4-(4-Cyano-3-methyl-phenoxy)-piperidine-1-carboxylic acid tert-butyl ester and 37 mL tert-Butyloxybis(dimethylamino)methane were allowed to react according to GP B to give 17 g (73%) 4-[4-Cyano-3-((E)-2-dimethylamino-vinyl)-phenoxy]-piperidine-1-carboxylic acid tert-butyl ester. m.p.: 135-137° C. (EtOH).

General Procedure (GP) Step C:

The appropriate N-heterocycloalkoxy-2-((E)-2-dimethylamino-vinyl)-benzonitrile (VI) was dissolved in methanolic HCl and the mixture was refluxed until the reaction was complete. After cooling and partial evaporation of the solvent the desired N-heterocycloalkoxy-2H-isoquinolin-1-one precipitated as hydrochloride from the solution and was isolated by filtration. Alternatively, the reaction mixture was evaporated to dryness and the crude product was purified by chromatography and afterwards converted into the hydrochloride by twice taking it up in 1M HCl and lyophilization.

C1) 15.2 g 4-(1-Benzyl-pyrrolidin-3-yloxy)-2-((E)-2-dimethylamino-vinyl)-benzonitrile in 140 mL methanolic HCl were allowed to react according to GP C to give 4.9 g (41%) 6-(1-Benzyl-pyrrolidin-3-yloxy)-2H-isoquinolin-1-one hydrochloride over two steps. Mass: Calcd. $(C_{20}H_{20}N_2O_2)$=320; found: 321 $(M+H^+)$.

The product thus obtained can be further modified by removing the protection using known conditions, such as hydrogenolysis on Pd/C.

C2) 13.3 g 3-[4-Cyano-3-((E)-2-dimethylamino-vinyl)-phenoxy]-piperidine-1-carboxylic acid tert-butyl ester in 140 mL methanolic HCl were allowed to react according to GP C to give 5.1 g (52%) 6-(Piperidin-3-yloxy)-2H-isoquinolin-1-one hydrochloride over two steps. Mass: Calcd. $(C_{14}H_{16}N_2O_2)$=244 found: 245 $(M+H^+)$.

C3) 13.9 g 4-(1-Benzhydryl-azetidin-3-yloxy)-2-((E)-2-dimethylamino-vinyl)-benzonitrile in 100 mL methanolic HCl were allowed to react according to GP C to give 4.5 g (32%) 6-(1-Benzhydryl-azetidin-3-yloxy)-2H-isoquinolin-1-one hydrochloride over two steps. Mass: Calcd. $(C_{25}H_{22}N_2O_2)$=382; found: 383 $(M+H^+)$. The product thus obtained can be further modified by removing the protection using known conditions, such as hydrogenolysis on Pd/C.

C4) 25 g 4-[4-Cyano-3-(E)-2-dimethylamino-vinylphenoxy]-piperidine-1-carboxylic acid tert-butyl ester in 300 mL methanolic HCl were allowed to react according to GP C to give 9.6 g (51%) 6-(Piperidin-4-yloxy)-2H-isoquinolin-1-one hydrochloride. Mass: Calcd. $(C_{14}H_{16}N_2O_2)$=244 found: 245 $(M+H^+)$.

What is claimed is:

1. A process for the preparation of a compound of formula (I)

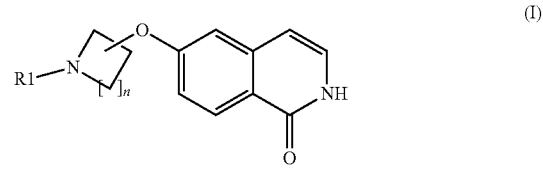

or a salt thereof,
wherein
n is 1, 2, 3 or 4; and
R1 is H or a protecting group,
comprising the steps of
(A) reacting a compound of formula (II)

wherein X is halogen,
in a suitable solvent and in the presence of a base selected from a tertiary alkali metal alkoxide, alkali metal hydride or alkali metal with a compound of formula (III)

wherein
R1 is H or a protecting group and
n is 1, 2, 3 or 4,
to give a compound of formula (IV)

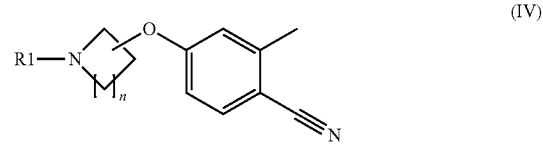

wherein
R1 is H or a protecting group and
n is 1, 2, 3 or 4;
and, if R1 is H, protecting the amino group to give a compound of formula (IV) wherein R1 is a amino protecting group;
(B) reacting a compound of formula (IV) with a compound of formula (V)

$$R_4\text{—}CH[N(R_5)_2]_2 \qquad (V)$$

wherein
R₄ is —O(C₁-C₆)alkyl, and
R₅ is (C₁-C₆)alkyl,
to yield a compound of formula (VI)

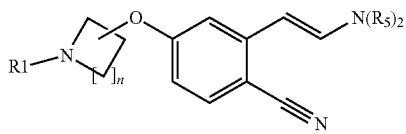

wherein R1 is a protecting group and
n is 1, 2, 3 or 4; and
(C) cyclizing a compound of formula (VI) and optionally removing the protecting group in a suitable solvent and in the presence of a hydrohalic acid to give a compound of formula (I)

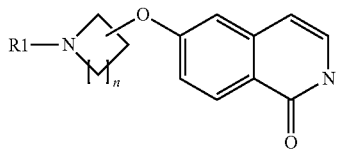

wherein R1 is H or a protecting group;

(D) optionally removing the protecting group from a compound of formula (I) obtained in step (C), wherein R1 is a protecting group, to give compound a formula (I) wherein R1 is H, and (E) optionally converting a compound of formula (I) into a salt thereof.

2. The process according to claim 1, wherein X is fluoro.

3. The process according to claim 1, wherein the base used in step (A) is selected from a tertiary alkali metal alkoxide.

4. The process according to claim 3, wherein the base is potassium tert-amylate or potassium tert-butoxide.

5. The process according to claim 1, wherein R4 in reagent (V) is tert-butyloxy or ethoxy.

6. The process according to claim 1, wherein R5 in reagent (V) is methyl.

7. The process according to claim 5, wherein reagent (V) used in step (B) is tert-butoxy-bis-(dimethylamino)methane.

8. The process according to claim 1, wherein the hydrohalic acid used in the cyclization reaction in step (C) is HCl.

9. The process according to claim 1, wherein n is 3.

10. The process according to claim 1, wherein the protecting group is an acid-labile group.

11. The process according to claim 1, wherein the protecting group in R1 is tert-butoxycarbonyl.

* * * * *